US009827279B2

(12) United States Patent
Yamamoto et al.

(10) Patent No.: US 9,827,279 B2
(45) Date of Patent: Nov. 28, 2017

(54) XANTHINE OXIDASE INHIBITOR AND URIC ACID PRODUCTION INHIBITOR

(75) Inventors: Naoki Yamamoto, Haga-gun (JP);
Isamu Watanabe, Haga-gun (JP);
Atsushi Suzuki, Haga-gun (JP);
Kohjiro Hashizume, Haga-gun (JP)

(73) Assignee: Kao Corporation, Tokyo (JP)

( * ) Notice: Subject to any disclaimer, the term of this patent is extended or adjusted under 35 U.S.C. 154(b) by 702 days.

(21) Appl. No.: 13/001,814

(22) PCT Filed: Jul. 7, 2009

(86) PCT No.: PCT/JP2009/062391
§ 371 (c)(1),
(2), (4) Date: Jun. 29, 2015

(87) PCT Pub. No.: WO2010/005004
PCT Pub. Date: Jan. 14, 2010

(65) Prior Publication Data
US 2011/0165274 A1    Jul. 7, 2011

(30) Foreign Application Priority Data

Jul. 7, 2008  (JP) ................. 2008-177016
Jul. 7, 2008  (JP) ................. 2008-177017

(51) Int. Cl.
*A61K 36/899*   (2006.01)
*A61K 36/00*    (2006.01)
*A23L 33/105*   (2016.01)

(52) U.S. Cl.
CPC ............ *A61K 36/00* (2013.01); *A23L 33/105* (2016.08); *A23V 2002/00* (2013.01)

(58) Field of Classification Search
CPC .................................................. A61K 36/899
See application file for complete search history.

(56) References Cited

U.S. PATENT DOCUMENTS

| 6,586,020 | B1 | 7/2003 | Breton et al. |
| 2005/0100622 | A1* | 5/2005 | Nair .................. A61K 36/185 424/777 |
| 2006/0216362 | A1 | 9/2006 | Enoki et al. |
| 2007/0154575 | A1 | 7/2007 | Shimoda et al. |

FOREIGN PATENT DOCUMENTS

| EP | 2 251 024 A1 | 11/2010 |
| JP | 10-095732 A | 4/1998 |
| JP | 11-180880 | 7/1999 |
| JP | 2001-163794 | 6/2001 |
| JP | 2002-121145 A | 4/2002 |
| JP | 2002-241299 | 8/2002 |
| JP | 2002-322055 | 11/2002 |
| JP | 2003-252776 A | 9/2003 |
| JP | 2004-123630 | 4/2004 |
| JP | 2004-250445 | 9/2004 |
| JP | 2005-350419 | 12/2005 |
| JP | 2006-036787 A | 2/2006 |
| JP | 2006-096666 | 4/2006 |
| JP | 2006-137679 | 6/2006 |
| JP | 2006-182732 A | 7/2006 |
| JP | 2006-213608 | 8/2006 |
| JP | 2006-519231 A | 8/2006 |
| JP | 2006-520803 | 9/2006 |
| JP | 2006-290802 | 10/2006 |
| JP | 2006-296226 | 11/2006 |
| JP | 2007-045814 | 2/2007 |
| JP | 2007-049955 | 3/2007 |
| JP | 2007-210993 | 8/2007 |
| JP | 2007-261987 | 10/2007 |
| JP | 2007-284397 | 11/2007 |
| JP | 2009-184992 A | 8/2009 |
| WO | WO 03/075685 A2 * | 9/2003 |
| WO | WO 2004/075844 A2 | 9/2004 |
| WO | WO 2004/084829 A2 | 10/2004 |
| WO | WO 2004/100969 A1 | 11/2004 |
| WO | WO 2005/085223 A1 | 9/2005 |
| WO | WO 2007/119837 | 10/2007 |

OTHER PUBLICATIONS

KFDA Korea Food Additives Code, accessed on May 13, 2013 achived to Apr. 21, 2008 using www.archive.org having the following archived URL: http://web.archive.org/web/20080421070030/http://fa.kfda.go.kr/standard/egongjeon_standard_view.jsp?SerialNo=6&GoCa=2> 2 pages.*
Deosthale et al. The Effect of Molybdenum Levels in Sorghum (Sorghum Vulgare Pers.) on Uric Acid and Copper Excretion in Man; Br. J. Nutrition (1974), 31, pp. 351-355.*
Huang et al. Effects of Genistein, Apigenin, Quercetin, Rutin and Astilbin on Serum Uric Acid Levels and Xanthine Oxidase Activities in Normal and Hyperuricemic Mice; Food and Chemical Toxicology; 49 (2011) 1943-1947.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Yasir et al. Hyperuricemia Treatment & Management; MedScape, Online, URL<http://emedicine.medscape.com/article/241767-treatment> Nov. 16, 2012, 4 pages.*

(Continued)

*Primary Examiner* — Chris R Tate
(74) *Attorney, Agent, or Firm* — Sterne, Kessler, Goldstein & Fox P.L.L.C.

(57) ABSTRACT

A xanthine oxidase inhibitor and a uric acid-producing inhibitor, each containing an extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L.

9 Claims, 3 Drawing Sheets (56) References Cited

OTHER PUBLICATIONS

Website document entitled "Sorghum bicolor". 2011. 1 page. Obtained from http://prgdb/crg.eu/wiki/Species:Sorghum_bicolor.*

International Search Report for PCT/JP2009/062391, I.A. fd: Jul. 7, 2009, dated Oct. 6, 2009 from the Japanese Patent Office, Tokyo, Japan.

International Preliminary Report on Patentability, Chapter I of the Patent Cooperation Treaty, including the Written Opinion for PCT/JP2009/062391, I.A. fd: Jul. 7, 2009, dated Jan. 5, 2011 from the International Bureau of WIPO, Geneva, Switzerland.

Alderman, MH et al., "Serum Uric Acid and Cardiovascular Events in Successfully Treated Hypertensive Patients," Hypertension, Jul 1999; 34: 144-150, American Heart Association, Dallas, TX.

Bao, L et al., "Protective effects of bilberry (*Vaccinium myrtillus* L.) extract on KBrO3-induced kidney damage in mice," J Agric Food Chem, Jan. 2008; 56(2): 420-425, American Chemical Society, Washington, DC.

Costantino, L et al., "Activity of polyphenolic crude extracts as scavengers of superoxide radicals and inhibitors of xanthine oxidase," Planta Med, Aug. 1992; 58(4): 342-344, Stuttgart, New York.

Duke, JA, "Gout." Duke Green Pharmacy, pp. 238-241 (Oct. 2001), translation by Kazuo Hoshiai, Kabushiki Kaisha Kenko Sangyo Shimbunsha, Health Industry Newspaper Publisher Co., Ltd., Tokyo, Japan.

Fang, J., "Serum Uric Acid and Cardiovascular Mortality: The NHANES I Epidemiologic Follow-up Study, 1971-1992," JAMA, May 2000; 283: 2404-2410, Am. Med. Assoc., Chicago, IL.

Feig, DI, et al., "Hypothesis: Uric acid, nephron number, and the pathogenesis of essential hypertension," Kidney Int, Jul. 2004; 66(1): 281-287, Springer-Verlag, New York.

Franse, LV et al., "Serum Uric Acid, Diuretic Treatment and Risk of Cardiovascular Events in the Systolic Hypertension in the Elderly Program (SHEP)," J Hypertens, Aug. 2000; 18(8): 1149-1154, Lippincott Williams & Wilkins, London, England.

Haig, A, "On Uric Acid and Arterial Tension," Br Med J, Feb. 1889; 1: 288-291, British Medical Assn, London, England.

Hakoda, M et al., "Serum uric acid concentration as a risk factor for cardiovascular mortality: a longterm cohort study of atomic bomb survivors," J Rheumatol, May 2005; 32: 906-912, Journal of Rheumatology Publishing Co, Toronto, Canada.

Richard J. Johnson, RJ et al., "Resurrection of Uric Acid as a Causal Risk Factor in Essential Hypertension," Hypertension, Jan. 2005; 45: 18-20, American Heart Association, Dallas, TX.

Lavelli, V et al., "Secoiridoids, tocopherols, and antioxidant activity of monovarietal extra virgin olive oils extracted from destoned fruits," J Agric Food Chem, Feb. 2005; 53(4): 1102-1107, Am. Chem. Soc., Washington, DC.

Ogasawara, M et al., Exercise-Induced Prolonged Hyperuricemia by Continuous Production and Release of Hypoxanthine in Fast-Twitch Muscle in Rats, Purine and Pyrimidine Metabolism 18: 1-10 (1994).

Tomita, M et al., "Effect of the change in Serum Uric Acid Levels on Mortality: A Prospective Cohort Study," Purine and Pyrimidine Metabolism 22: 133-139 (1998).

Verdecchia, P et al., "Relation Between Serum Uric Acid and Risk of Cardiovascular Disease in Essential Hypertension : The PIUMA Study," Hypertension, Dec. 2000; 36: 1072-1078, American Heart Association, Dallas, TX.

Yun, KW et al., "The Influence of the Growth Season on the Antimicrobial and Antioxidative Activity in *Artemisia princeps* var. *orientalis*," Industrial Crops and Products 27:69-74 (2008), Elsevier, New York.

Formulation AA11/886, Dawa Bara-e-Niqris Haar, India Traditional Knowledge Database Library (TKDL) extract, English translation and terminology conversion of Kitaab-al-Haawi-fil-Tibb, vol. XI (9$^{th}$ century AD), by Abu Bakr Mohammad.Bin Zakariyya Al-Razi, Dayerah-al-Ma'aarif Usmania, Hyderabad, (First Ediction), 1962, p. 248.

Formulation PD04/24, Ratha Pithathirkku Kudineer, India Traditional Knowledge Database Library (TKDL) extract, English translation and terminology conversion of Agathiar vaithiam by Agasthiyar 600.Pub& Ed. Anonymous, p. 25.

Formulation AH1/489, Akar-ul-Zait, India Traditional Knowledge Database Library (TKDL) extract, English translation and terminology conversion of Al-Qaanoon-fil-Tibb, vol. II (11$^{th}$ century AD), by Abu Ali Ibn-e-Sina; Institute of History of Medicine and Medical Research, Jamia Hamdard, New Delhi-62, 1987, p. 284.

Formulation MH1/3576, Maa-ul Usool Bara-e-Niqris, India Traditional Knowledge Database Library (TKDL) extract, English translation and terminology conversion of; Ilaaj-al-Amraaz (18$^{th}$ century AD) by Mohammad Shareef Khan, Afzal-al-Matabe, Barqi Press, Delhi, 1921, p. 308.

Formulation AH2/340, Milh-e-Mushil, India Traditional Knowledge Database Library (TKDL) extract, English translation and terminology conversion of Al-Qaanoon-fil-Tibb, vol. V (11th century AD), by Abu Ali Ibn-e-Sina, Publication Department, Jamia Hamdard, New Delhi-62, 1996, p. 142.

Formulation BA4/434, Nuskha-e-jullab, India Traditional Knowledge Database Library (TKDL) extract, English translation and terminology conversion of Mohammad Azam Khan; Ikseer Azam, vol. IV (19$^{th}$ century AD), Matba Nizami, Kanpur, 1872, p. 38.

Minton, B.L., "Celery Works Great for Inflammation, Gout, Cancer, and High Blood Pressure," Natural News.com, Sep. 10, 2008, http://www.naturalnews.com/024135_cancer_celery_inflammation.html.

Justesen, U. et al., "Composition of flavonoids in fresh herbs and calculation of flavonoid intake by use of herbs in traditional Danish dishes," Food Chemistry 73: 345-350 (May 2001), Elsevier Science Ltd., Barking, England.

Huang, J et al., "Effects of genistein, apigenin, quercetin, rutin and astilbin on serum uric acid levels and xanthine oxidase activities in normal and hyperuricemic mice," Food Chem Toxicol 49(9): 1943-1947, (Sep. 2011), Elsevier Science Ltd., Exeter, England.

CAplus$^{SM}$ No. 2007:452123—abstract and bibliographic data for: Jirovetz, L et al., "Spice plants: chemical composition and antioxidant properties of Pimenta Lindl. Essential oils. Part 1: Pimenta dioica (L.) Merr. Leaf oil from Jamica," Ernaehrung (Vienna, Austria) 31: 55-62 (2007), Fachzeitschriftenverlagsgesellschaft mbH, Austria, printed Sep. 25, 2013, from stnwcb-jpo-b.cas.org.

Da Silva, SL et al., "The influence of electronic, steric and hydrophobic properties of flavonoicl compounds in the inhibition of the xanthine oxidase," J. Molec Structure (Theochem) 684 (2004) 1-7, Elsevier, Amsterdam, Netherlands.

Notification of Second Office Action for CN Patent Appl. No. 200980126041.2, dated Aug. 20, 2012, from the Patent Office of the People's republic of China, Beijing, China.

Lin, CM et al., "Molecular modeling of flavonoids that inhibits xanthine oxidase," Biochem Biophys Res Commun, May 2002; 294(1): 167-172, Academic Press, USA.

Zhang, Zap-jun et al., "Development and Utilization of Natural Pigment Kaoliang Color," Cereals and Oils, 2005; 5:40-41, China Academic J Electronic Publishing House, Beijing, China.

Kanatani, Daisuke et al., "Anti-oxidation Activity of Eugenol," Foreign Medical Sciences: Traditional Chinese Medicine Fascicule 27(4): 247 (2005) , China Acad J Electronic Publishing House, Beijing, China.

Kimura, Susumu et al., "Easy Processing for Various Types of Food," Edition 1, Chinese Food Publishing Company, p. 140 (1988), China.

Pan, Shiquan et al., "Bright Prospect of Utilization of Natural Pigment Kaoliang Color," Liaoning Agricultural Science, (1994), No. 3, p. 50-51, Liaoning Provincial Academy of Agricultural Sciences and Agricultural Society of Liaoning Province, China.

Extended European search report for EP Application No. 09794448.2, including the supplementary European search report and the European search opinion, dated Mar. 18, 2015, European Patent Office, Munich, Germany.

\* cited by examiner

XANTHINE OXIDASE INHIBITOR AND URIC ACID PRODUCTION INHIBITOR

TECHNICAL FIELD

The present invention relates to a xanthine oxidase inhibitor and a uric acid-producing inhibitor.

BACKGROUND ART

Uric acid is a metabolic product originating from nucleic acids as a carrier of genetic information or ATP as a carrier of energy, and it is secreted as a final degradation product of purine compounds in mammals, etc. Regarding the mechanism of this metabolism, hypoxanthine is converted into xanthine, and then xanthine is converted into uric acid. This reaction is catalyzed by a xanthine oxidase.

When an abnormality in the metabolism of purine compounds by xanthine oxidase occurs, various disorders are caused. As an example, hyperuricemia can be mentioned (Non-Patent Literature 1). In general, saturation solubility of sodium urate in blood serum is believed to be 7 mg/dL at 37° C. Thus, when the blood uric acid concentration is more than 7 mg/dL, there is a possibility that crystals of uric acid are precipitated in a human body. Accordingly, a symptom in which the blood uric acid concentration is more than 7 mg/dL is called "hyperuricemia." In addition, the abnormality in the metabolism of purine compounds may also cause gout. When the blood uric acid concentration stays continuously high, crystals of uric acid salt accumulate within or around a joint. Due to such phenomenon, a symptom like occurrence of acute arthritis, gouty node, joint dysfunction and joint deformation, etc. is caused. Such symptom is called "gout," which is a disorder capable of causing various complications like renal dysfunction and vascular dysfunction, etc. In addition, it is known that uric acid is a risk factor for cardiovascular diseases (Non-Patent Literatures 2 to 7) and a cardiovascular disease such as hypertension is caused by the increase in value of uric acid in blood (Non-Patent Literatures 8 to 11).

Conventionally, the number of patients suffering from gout and hyperuricemia is not so high in Japan. As such, not so much attention has been paid to prevention of gout and hyperuricemia. However, in recent years, a rapid change occurs in lifestyle and the number of people who eat high calorie, high protein and high fat foods is on the rise. Furthermore, an increasing number of onset of gout is reported according to increased stress, etc. Thus, greater attention is now being paid to the prevention and amelioration of gout or hyperuricemia, which is a risk factor thereof.

Until now, in order to improve or prevent hyperuricemia, gout, or a cardiovascular disease that is caused by high content value of uric acid in blood, "Probenecid (trade name)" as a uricosuric drug or "Allopurinol (trade name)" as a uric acid-producing inhibitor has been provided. However, those are problematic in that they are transient, and side effects like gastric dysfunction, rash, decrease in white blood cells, decrease in platelets, hepatic dysfunction and renal dysfunction, etc. are accompanied therewith.

As such, in order to prevent or improve the disorders described above, there is a need to control or reduce the value of uric acid in blood to an appropriate level by inhibiting the production of uric acid in a living body.

PRIOR ART LITERATURE

Non-Patent Literatures

Non-Patent Literature 1: Ogasawara Masashi et al., "Purine and Pyrimidine Metabolism", 1994, Vol. 18, No. 1, p. 1-10

Non-Patent Literature 2: Franse L. V. et al., "J Hypertens", 2000, Vol. 18, p. 1149-1154

Non-Patent Literature 3: Fang J. et al., "JAMA", 2000, Vol. 283, No. 18, p. 2404-2410

Non-Patent Literature 4: Tomita Masako, et al., "Purine and Pyrimidine Metabolism", 1998, Vol. 22, No. 1, p. 133-139

Non-Patent Literature 5: Hakoda M. et al., "J Rheumatol", 2005, Vol. 32, p. 906-912

Non-Patent Literature 6: Alderman M. H. et al., "Hypertention", 1999, Vol. 34, p. 144-150

Non-Patent Literature 7: Verdecchia P. et al., "Hypertention", 2000, Vol. 36, p. 1072-1078

Non-Patent Literature 8: Johonson R. J. et al., "Hypertention", 2005, Vol. 45, p. 18-20

Non-Patent Literature 9: Feig D. I. et al., "Kidney Int", 2004, Vol. 66, p. 281-287

Non-Patent Literature 10: Mahomed F. A., "Lancet", 1879, Vol. 1, p. 399-401

Non-Patent Literature 11: Haig A. et al., "British Medical Journal", 1889, Vol. 1, p. 288-291

SUMMARY OF INVENTION

An object of the present invention is to provide a xanthine oxidase inhibitor having an excellent inhibitory effect on xanthine oxidase. Another object of the present invention is to provide a uric acid-producing inhibitor having an excellent inhibitory effect on uric acid production. Further object of the present invention is to provide an agent for improving or preventing gout, hyperuricemia or a cardiovascular disease which is effective, highly safe and free of any side effect even when it is continuously used, and has an effect of improving or preventing gout, hyperuricemia or a cardiovascular disease. Yet further object of the present invention is to provide a food product or a beverage which has an inhibitory effect on xanthine oxidase, an inhibitory effect on production of uric acid and/or an effect of improving or preventing gout, hyperuricemia or a cardiovascular disease.

In view of the problems described above, inventors of the present invention found that an extract from specific plant species inhibits production of uric acid which is catalyzed by xanthine oxidase and has an inhibitory effect on xanthine oxidase. The present invention was completed based on this finding.

The present invention resides in a xanthine oxidase inhibitor, comprising an extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L.

Further, the present invention resides in a uric acid-producing inhibitor, comprising an extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illi-* cium verum, Canavalia gladiata, Hyssopus officinalis, Ribes nigrum, Vaccinium myrtillus, Artemisia princeps and Haematoxylon campechianum L.

Furthermore, the present invention resides in an agent for improving or preventing gout or hyperuricemia, comprising an extract from at least one member selected from the group consisting of Zanthoxylum bungeanum, Sorghum nervosum, Cuminurn cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L.

Furthermore, the present invention resides in an agent for improving or preventing a cardiovascular disease, comprising an extract from at least one member selected from the group consisting of Zanthoxylum bungeanum, Sorghum nervosum, Cuminum cyminum and Rosa centifolia.

Furthermore, the present invention resides in a food product or a beverage, comprising, as an effective component, an extract from at least one member selected from the group consisting of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L.

Furthermore, the present invention resides in use of an extract from at least one member selected from the group consisting of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L. as a xanthine oxidase inhibitor, a uric acid-producing inhibitor, an inhibitor against increase in value of blood uric acid or a preventing agent against onset possibility of gout or hyperuricemia.

Furthermore, the present invention resides in use of an extract from at least one member selected from the group consisting of Zanthoxylum bungeanum, Sorghum nervosum, Cuminum cyminum and Rosa centifolia as a preventing agent against onset possibility of a cardiovascular disease.

Furthermore, the present invention resides in an extract from at least one member selected from the group consisting of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L. for use in the improvement or prevention of gout or hyperuricemia.

Furthermore, the present invention resides in an extract from at least one member selected from the group consisting of Zanthoxylum bungeanum, Sorghum nervosum, Cuminum cyminum and Rosa centifolia for use in the improvement or prevention of a cardiovascular disease.

Furthermore, the present invention resides in a method of inhibiting a xanthine oxidase, inhibiting production of uric acid, inhibiting an increase in a value of blood uric acid, or improving or reducing onset probability of gout or hyperuricemia, which comprises administering an extract from at least one member selected from the group consisting of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L.

Still furthermore, the present invention resides in a method of improving a cardiovascular disease or reducing onset possibility of the disease, which comprises administering an extract from at least one member selected from the group consisting of Zanthoxylum bungeanum, Sorghum nervosum, Cuminum cyminum and Rosa centifolia.

The xanthine oxidase inhibitor of the present invention has an excellent inhibitory effect on an activity of xanthine oxidase. Furthermore, the uric acid-producing inhibitor of the present invention has an excellent inhibitory effect on uric acid production. Furthermore, the agent for improving or preventing gout, hyperuricemia or a cardiovascular disease of the present invention is effective, highly safe and free of any side effect even when it is continuously used, and therefore has an effect of improving or preventing gout, hyperuricemia or a cardiovascular disease. Still furthermore, the food product and the beverage of the present invention have an inhibitory effect on xanthine oxidase, an inhibitory effect on production of uric acid, and/or an effect of improving or preventing gout, hyperuricemia or a cardiovascular disease.

Other and further features and advantages of the invention will appear more fully from the following description, appropriately referring to the accompanying drawings.

MODE FOR CARRYING OUT THE INVENTION

A xanthine oxidase inhibitor and a uric acid-producing inhibitor according to the present invention comprises an extract from at least one member selected from the group consisting of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L. These extracts are originated from natural products. In addition, they are the extracts of those which have been conventionally ingested as herb medicine and a spice, etc. Thus, the xanthine oxidase inhibitor and uric acid-producing inhibitor of the present invention have no side effects even when they are continuously used, and they are useful as a highly safe pharmaceutical agent, a food product or a beverage which has an effect of improving or preventing gout, hyperuricemia or a cardiovascular disease.

In the present invention, *Zanthoxylum bungeanum* is a deciduous shrub belonging to genus *Zanthoxylum* in the Rutaceae family, native to China. Conventionally, a herb medicine containing seeds of *Zanthoxylum bungeanum* as a raw material has been mainly used as a common drug for stomachache or diarrhea.

In the present invention, *Sorghum nervosum* is an annual plant belonging to genus *Sorghum* in the Poaceae family, native to tropical Africa. Conventionally, *Sorghum nervosum* has been mainly used as grains, raw materials for producing alcohol, and coloring materials.

In the present invention, *Cuminum cyminum* is an annual plant belonging to genus *Cuminum* in the Apiaceae family, native to Egypt, etc. Conventionally, *Cuminum cyminum* has been mainly used as a spice.

In the present invention, *Rosa centifolia* is a plant belonging to genus *Rosa* in the Rosaceae family, native to France, etc. Conventionally, *Rosa centifolia* has been mainly used as an ornamental plant or a raw material for preparing perfume. Specifically, petals of pink rose or the like are used as an example of the *Rosa centifolia*.

In the present invention, *Pimenta officinalis* indicates fruits or leaves of an evergreen high tree belonging to genus *Pimenta* in the Myrtaceae family, which is called "allspice" and native to Jamaica. Conventionally, it has been mainly used as a spice.

In the present invention, *Origanum majorana* is a perennial plant belonging to genus *Origanum* in the Lamiaceae family, native to Egypt. Conventionally, *Origanum majorana* has been mainly used as a spice.

In the present invention, *Psidium guajava* is a tropical evergreen shrub belonging to genus *Psidium* in the Myrtaceae family native to Mexico and the tropical United States.

In the present invention, *Pimpinella anisum* is an annual plant belonging to genus *Pimpinella* in the Apiaceae family, native to eastern mediterranean region including Greece and Egypt, etc. The *Pimpinella anisum* seed (also known as "aniseed"), which is the fruit of the plant, is mainly used as a spice and perfume.

In the present invention, *Olea europaea* is an evergreen high tree belonging to genus *Olea* in the Oleaceae family, native to mediterranean coast region. Fruits of the plant (i.e., sarcocarp and seeds) are used as a raw material for olive oil.

In the present invention, *Illicium verum* is an evergreen high tree belonging to genus *Illicium* in the Illiciaceae family, native to China. Dried fruits of the plant are mainly used as a spice which is called "star anise."

In the present invention, *Canavalia gladiata* is an annual plant belonging to genus *Canavalia* in the Fabaceae family, which is also known "sword bean" and cultivated in tropical Asia region, etc. The *Canavalia gladiata* is used as an oriental medicine, a health food product and a health tea.

In the present invention, *Hyssopus officinalis* is a semi-evergreen shrub belonging to genus *Hyssopus* in the Lamiaceae family, native to Europe and Southeastern Asia. *Hyssopus officinalis* is mainly used as aroma oil.

In the present invention, *Ribes nigrum* is a deciduous shrub belonging to genus *Ribes* in the Grossulariaceae family, which is native to Europe and Central Asia and also referred to as cassis. Fruits of the plant are mainly used as food.

In the present invention, *Vaccinium myrtillus* is a deciduous shrub belonging to genus *Vaccinium* in the Ericaceae family, which is native to North America and also referred to as Bilberry. *Vaccinium myrtillus* is mainly consumed as a raw food or used for producing a processed food product, etc.

In the present invention, *Artemisia princeps* is a perennial plant belonging to genus *Artemisia* in the Asteraceae family, which is native to Japan and Korean Peninsula and also referred to mugwort. Conventionally, *Artemisia princeps* has been mainly used as a food material.

In the present invention, *Haematoxylon campechianum* L. is an evergreen medium-height tree belonging to genus *Haematoxylon* in the Caesalpiniaceae family, native to Mexico, and it is also called "logwood." *Haematoxylon campechianum* L. is mainly used as a source for obtaining honey, a dye, a pigment and an ink, etc.

According to the present invention, any part of the plants described above can be used. For example, one or a plurality of any parts like the whole tree, whole plant, roots, tubers, trunks, branches, stems, leaves, tree barks, tree sap, tree lipids, flowers, petals, flower buds, fruits, pericarps, husks, seeds, shells, sprouts, flower spikes and core materials and a combination thereof can be used.

In the present invention, it is preferable that seeds of *Zanthoxylum bungeanum* be used to obtain the extract of *Zanthoxylum bungeanum*.

In the present invention, it is preferable that fruits or husks of *Sorghum nervosum* be used to obtain the extract of *Sorghum nervosum*. It may be possible to use commercially available *Sorghum nervosum* pigment (for example, the *Sorghum nervosum* pigment manufactured by OCI Co., Ltd.) as the extract of *Sorghum nervosum*.

In the present invention, it is preferable that seeds of *Cuminum cyminum* be used to obtain the extract of *Cuminum cyminum*.

In the present invention, it is preferable that petals or flower buds of *Rosa centifolia* be used to obtain the extract of *Rosa centifolia*.

In the present invention, it is preferable that fruits and/or leaves of *Pimenta officinalis* be used to obtain the extract of *Pimenta officinalis*.

In the present invention, it is preferable that leaves and/or above-ground parts of *Origanum majorana* be used to obtain the extract of *Origanum majorana*.

In the present invention, it is preferable that leaves, fruits and/or pericarps of *Psidium guajava* be used to obtain the extract of *Psidium guajava*.

In the present invention, it is preferable that fruits and/or seeds of *Pimpinella anisum* be used to obtain the extract of *Pimpinella anisum*.

In the present invention, it is preferable that fruits, seeds and/or leaves of
*Olea europaea* be used to obtain the extract of *Olea europaea*. It is particularly preferable that the leaves be used for extraction.

In the present invention, it is preferable that pericarps, fruits and/or seeds of *Illicium verum* be used to obtain the extract of *Illicium verum*.

In the present invention, it is preferable that above-ground parts of a *Canavalia gladiata* be used to obtain the extract of *Canavalia gladiata*. It is particularly preferable that the shells and/or seeds be used for extraction.

In the present invention, it is preferable that above-ground parts like leaves, stems, sprouts, flowers and the like of *Hyssopus officinalis* be used to obtain the extract of *Hyssopus officinalis*. It is particularly preferable that the leaves of *Hyssopus officinalis* be used for extraction.

In the present invention, it is preferable that leaves, fruits and/or seeds of *Ribes nigrum* be used to obtain the extract of *Ribes nigrum*. It is particularly preferable that the fruits of *Ribes nigrum* be used.

In the present invention, it is preferable that above-ground parts of *Vaccinium myrtillus* be used to obtain the extract of *Vaccinium myrtillus*. It is particularly preferable that the leaves, fruits, pericarps and/or seeds of *Vaccinium myrtillus* be used for extraction.

In the present invention, it is preferable that above-ground parts including whole plant like leaves, stems, sprouts and flower spikes, etc. of *Artemisia princeps* be used to obtain the extract of *Artemisia princeps*. It is particularly preferable that the leaves of *Artemisia princeps* be used for extraction.

In the present invention, it is preferable that above-ground parts of *Haematoxylon campechianum* L. be used to obtain the extract of *Haematoxylon campechianum* L.

A method of producing an extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* or *Haematoxylon campechianum* L. for use in the present invention is not specifically limited. By performing extraction with the plant based on an ordinary method in the art, the extract can be obtained.

Specifically, juice obtained by subjecting dried products of the plants, smashed products thereof or the plants themselves to pressure-extraction, a crude extract obtained by using water or an organic solvent such as alcohol, ether and acetone, and an extraction fraction that is obtained by purifying the crude extract by distribution or various chromatographies like column chromatography, etc. may be used as the extract in the present invention. These can be used singly or in combination of two or more. In the present invention, it is preferable to use an extract which is obtained from a dried product obtained by drying the plant or smashed product thereof by using water, alcohol or their mixture.

The extraction time and extraction temperature required for obtaining the extract for use in the present invention are not specifically limited. With respect to the extraction time, it is preferably 30 minutes to 20 days, and more preferably 1 day to 10 days. With respect to the extraction temperature, it is preferably 0 to 100° C. and more preferably 10 to 70° C.

The extract obtained from the plant may be used as it is as a xanthine oxidase inhibitor or a uric acid-producing inhibitor. Alternatively, it may be used as a xanthine oxidase inhibitor or a uric acid-producing inhibitor after it is added with an appropriate liquid or solid vehicle or an extender like titanium oxide, calcium carbonate, distilled water, lactose and starch. In addition, the extract may be used as an agent for inhibiting an increase in a value of blood uric acid, or a preventing agent against onset possibility of gout or hyperuricemia. In such case, the amount of the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* or *Haematoxylon campechianum* L. in the xanthine oxidase inhibitor, the uric acid-producing inhibitor, the agent for inhibiting an increase in value of blood uric acid or the preventing agent against onset possibility of gout or hyperuricemia is not specifically limited. However, in terms of solid content concentration, the extract is preferably contained in an amount of 0.001 to 100% by mass, more preferably 0.01 to 80% by mass, and still more preferably 0.1 to 80% by mass.

The extract of each of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. has an activity of inhibiting a xanthine oxidase and an activity of inhibiting uric acid production. As such, the extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. can be used as a pharmaceutical agent for the prevention of gout, hyperuricemia or a cardiovascular disease like hypertension, and the like, and reduction or improvement of their onset possibility. Furthermore, a food product and a beverage containing the extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. have an effect of inhibiting a xanthine oxidase, an effect of inhibiting uric acid production, an effect of inhibiting an increase in value of blood uric acid, and an effect of improving or preventing gout, hyperuricemia and a cardiovascular disease or reducing their onset possibility. It has never been known before that the extract of each of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. has an activity of inhibiting xanthine oxidase and an activity of inhibiting uric acid production, and it is first discovered by the inventors of the present invention.

The xanthine oxidase inhibitor and uric acid-producing inhibitor which contains, as an effective component, the extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. can be used as it is as the beverage or the food product of the present invention. Alternatively, they can be used as an additive or a blend preparation for a beverage or a food product. In the present invention, the additive or the blend preparation for a beverage or a food product indicates an additive or a blend preparation generally used for a beverage of a food product like a perfume, a pigment and an anti-oxidizing agent, that is mixed with the xanthine oxidase inhibitor or the uric acid-producing inhibitor which contains, as an effective component, the extract from at least one member selected from the group consisting of *Zanthoxylum bungeanum, Sorghum nervosum, Cuminum cyminum, Rosa centifolia, Pimenta officinalis, Origanum majorana, Psidium guajava,*

*Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L.

The xanthine oxidase inhibitor or the uric acid-producing inhibitor of the present invention may be used as it is as an agent for improving or preventing gout, hyperuricemia or a cardiovascular disease. Alternatively, by incorporating the xanthine oxidase inhibitor or the uric acid-producing inhibitor of the present invention as an effective component and mixing with other components, it may be used as an agent for improving or preventing gout, hyperuricemia or a cardiovascular disease.

By mixing the agent for improving or preventing gout, hyperuricemia or a cardiovascular disease of the present invention with an appropriate amount of the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and/or *Haematoxylon campechianum* L., and if necessary, with various additives, pharmaceutical agents of various formulations can be prepared. For example, it may be prepared as an orally administered drug like a tablet, a capsule, a granule, a powder, a syrup and an extract, or a parenterally administered drug like an ointment, an eye ointment, a lotion, a cream, a patch, a suppository, an eye drop, a nose drop and an injection solution. These pharmaceutical agents can be produced by using various additives according to an ordinary method. The additives used are not specifically limited and those that are commonly used may be used. Examples thereof include a solid carrier such as starch, lactose, white sugar, mannitol, carboxymethylcellulose, corn starch and inorganic salt; a liquid carrier such as distilled water, physiological saline, aqueous glucose solution, alcohol like ethanol, propylene glycol and polyethylene glycol; an oil carrier such as various animal or vegetable oils, white vaseline, paraffin and waxes; a stabilizing agent, a humidifying agent, an emulsifying agent, a binding agent, and an isotonic agent.

With respect to the agent for improving or preventing gout, hyperuricemia or a cardiovascular disease of the present invention, the mixing ratio of the extract is not particularly limited. In terms of solid content concentration, the extract is admixed in an amount of preferably 0.001 to 100% by mass, more preferably 0.01 to 80% by mass, and still more preferably 0.1 to 80% by mass.

The effective dosage of the agent for improving or preventing gout, hyperuricemia or a cardiovascular disease of the present invention is appropriately selected and determined based on age, body weight, symptom and condition of a patient, an administration route, an administration schedule, a preparation type, and strength of the inhibitory activity of a material, and the like. For oral administration, for example, it is preferably 0.001 to 10 g/kg of body weight per day in general. It can be also administered in several divided doses per day.

The xanthine oxidase inhibitor or uric acid-producing inhibitor which contains, as an effective component, the extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. can be used as it is as the beverage or the food product of the present invention. Furthermore, a food product or a beverage which contains, as an effective component, the xanthine oxidase inhibitor or uric acid-producing inhibitor which contains, as an effective component, the extract from at least one member selected from the group consisting of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. can provided. The food product or beverage of the present invention which contains the extract described above has an effect of inhibiting a xanthine oxidase, an effect of inhibiting uric acid production and an effect of inhibiting an increase in value of blood uric acid, as well as an effect of improving or preventing gout, hyperuricemia and a cardiovascular disease, and reducing their onset possibility. Thus, based on the idea of having an effect of inhibiting a xanthine oxidase, an effect of inhibiting uric acid production, an effect of inhibiting an increase in value of blood uric acid, an effect of improving or preventing gout, hyperuricemia or a cardiovascular disease, or reducing their onset possibility, the food product or beverage of the present invention containing the extract described above may be applied to a functional food and beverage product, a food and beverage product for a patient, and a special health food and beverage product in which the point of use is indicated, if necessary. Furthermore, the xanthine oxidase inhibitor and the uric acid-producing inhibitor of the present invention may be used for production of the functional food and beverage product, the food and beverage product for a patient, and the special health food and beverage product that are described above.

The food product containing the xanthine oxidase inhibitor or uric acid-producing inhibitor of the present invention as an effective component may be provided by adding an appropriate aiding agent to the xanthine oxidase inhibitor or uric acid-producing inhibitor containing, as an effective component, the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and/or *Haematoxylon campechianum* L., and by molding them using an ordinary means to a form suitable for eating, for example, a granule, a particle, a tablet, a capsule and a paste. Furthermore, the food product of the present invention can be provided as a candy, a troche, a gum, a yogurt, an ice cream, a pudding, a jelly, a sweet jelly of red beans and the like in which an appropriate amount of the xanthine oxidase inhibitor or uric acid-producing inhibitor of the present invention containing, as an effective component, the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and/or *Haematoxylon campechianum* L. is contained. These food products may be provided by an ordinary method with addition of various additives, if necessary.

The beverage of the present invention can be provided as an alcoholic drink, a coffee drink, a juice, a fruit juice drink, a soda drink, a cooling and refreshing drink, a milk, a whey beverage, a yogurt drink and the like in which an appropriate amount of the xanthine oxidase inhibitor or uric acid-producing inhibitor of the present invention containing, as an effective component, the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and/or *Haematoxylon campechianum* L. is contained. These beverages may be prepared by an ordinary method with addition of various additives, if necessary.

These food products or beverages which contain as an effective component the xanthine oxidase inhibitor or uric acid-producing inhibitor of the present invention may be produced according to an ordinary method by appropriately mixing additives generally used for a food product or a beverage like glucose, fructose, sucrose, maltose, sorbitol, stevioside, rubusoside, corn syrup, lactose, citric acid, tartaric acid, malic acid, succinic acid, lactic acid, L-ascorbic acid, dl-α-tocopheol, sodium erythorbate, glycerin, propylene glycol, glycerin fatty acid ester, polyglycerin fatty acid ester, sucrose fatty acid ester, sorbitan fatty acid ester, propylene glycol fatty acid ester, gum Arabic, carrageenan, casein, gelatin, pectin, agar, vitamin B groups, nicotinic acid amide, calcium pantothenate, amino acids, calcium salts, pigments, perfumes and preservatives.

With respect to the food product or beverage containing, as an effective component, the xanthine oxidase inhibitor or uric acid-producing inhibitor of the present invention, the mixing ratio of the extract of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* or *Haematoxylon campechianum* L. is not particularly limited. In terms of solid content concentration, the extract is admixed in an amount of preferably 0.001 to 100% by mass, more preferably 0.01 to 80% by mass, and still more preferably 0.1 to 80% by mass.

When a food product, a beverage or a pharmaceutical agent which contains, as an effective component, the xanthine oxidase inhibitor or uric acid-producing inhibitor of the present invention is to be prepared, other extracts which also exhibit an activity of inhibiting a xanthine oxidase or an activity of inhibiting uric acid production may be used together (for example, an extract of rosemary, peppermint or the like (see, JP-A-2003-252776)). In such case, the mixing ratio between the extract for use in the present invention and other extract is not specifically limited. However, in terms of the solid content of an extract (i.e., an extract component), it is generally from about 1:9 to 9:1 in mass ratio.

Examples

Hereinafter, the present invention will be described more in detail with reference to Examples, but it should be understood that the technological scope of the present invention is not particularly limited by the following Examples.

1. Preparation of Various Extracts (1) Preparation of *Cuminum cyminum* Extract

To 40 g of *Cuminum cyminum* seeds (obtained from SHINWA BUSSAN CO., LTD.), 400 mL of aqueous ethanol solution (50% by volume) was added, and then extraction was carried out for 14 days at room temperature under a stable condition. After that, the extract was obtained by performing filtration. The solid content concentration of the extract was 1.64% (w/v).

(2) Preparation of *Rosa centifolia* Extract

To 10 g of petals of pink rose (obtained from TOCHIMOTO TENKAIDO CO., LTD.), 100 mL of aqueous ethanol solution (50% by volume) was added, and then extraction was carried out for 7 days at room temperature under a stable condition. After that, the *Rosa centifolia* extract was obtained by performing filtration. The solid content concentration of the extract was 4.52% (w/v).

(3) Preparation of *Zanthoxylum bungeanum* Extract

To 10 g of seeds of *Zanthoxylum bungeanum* (obtained from TOCHIMOTO TENKAIDO CO., LTD.), 100 mL of aqueous ethanol solution (50% by volume) was added, and then extraction was carried out for 7 days at room temperature under a stable condition. After that, the *Zanthoxylum bungeanum* extract was obtained by performing filtration. The solid content concentration of the *Zanthoxylum bungeanum* extract was 2.24% (w/v).

(4) Preparation of *Sorghum nervosum* Extract

*Sorghum nervosum* pigment (obtained from OCI Co., Ltd.) was dissolved in an aqueous ethanol solution (50% by volume) to have 1% (w/v) concentration, and as a result, the *Sorghum nervosum* extract was prepared.

(5) Preparation of *Pimenta officinalis* Extract

To 10 g of fruit part of *Pimenta officinalis* (obtained from TOCHIMOTO TENKAIDO CO., LTD.), 100 mL of aqueous ethanol solution (50% by volume) was added, and then extraction was carried out for 7 days at room temperature under a stable condition. After that, the extract was obtained by performing filtration. The solid content concentration of the extract was 1.33% (w/v).

(6) Preparation of *Psidium guajava* Extract

The extract powder of *Psidium guajava* leaves (obtained from MATSUURA YAKUGYOU Co., Ltd.) was dissolved in an aqueous ethanol solution (20% by volume) to have the concentration of 1% (w/v), and as a result, the extract was obtained.

(7) Preparation of *Origanum majorana* Extract

To 10 g of above-ground parts of *Origanum majorana* (including leaves) (obtained from TOCHIMOTO TENKAIDO CO., LTD.), 100 mL of aqueous ethanol solution (50% by volume) was added, and then extraction was carried out for 7 days at room temperature under a stable condition. After that, the extract was obtained by performing filtration. The solid content concentration of the extract was 2.22% (w/v).

(8) Preparation of *Pimpinella anisum* Extract

To 10 g of seeds of *Pimpinella anisum* (obtained from TOCHIMOTO TENKAIDO CO., LTD.), 100 mL of aqueous ethanol solution (50% by volume) was added, and then extraction was carried out for 7 days at room temperature under a stable condition. After that, the extract was obtained by performing filtration. The solid content concentration of the extract was 1.12% (w/v). The extract was diluted with aqueous ethanol solution (50% by volume), to be 1.00% (w/v) of the solid content concentration.

(9) Preparation of *Olea europaea* Extract

The *Olea europaea* extract powder (obtained from NIPPON Funmatsu Yakuhin Co., Ltd.), which has been prepared by extraction from *Olea europaea* leaves with ethanol, was dissolved in an aqueous ethanol solution (40% by volume) to obtain the *Olea europaea* extract with a solid content concentration of 1.00% (w/v).

(10) Preparation of *Illicium verum* Extract

To 10 g of fruits of *Illicium verum* (star anise) (obtained from TOCHIMOTO TENKAIDO CO., LTD.), 100 mL of aqueous ethanol solution (50% by volume) was added, and then extraction was carried out for 7 days at room temperature under a stable condition. After that, the extract was obtained by performing filtration. The solid content concentration of the extract was 2.51% (w/v). The extract was diluted with aqueous ethanol solution (50% by volume), to be 1.00% (w/v) of the solid content concentration.

(11) Preparation of *Canavalia gladiata* Extract

To 10 g of *Canavalia gladiata* (obtained from SHINWA BUSSAN CO., LTD.), 100 mL of hot water was added, and then extraction was carried out for 7 hours at 70° C. After that, the liquid extract was obtained by performing filtration. The liquid extract was added with ethanol (99.5% by volume) to give an aqueous ethanol solution (10% by volume). The solid content concentration of this liquid extract was 0.76% (w/v).

(12) Preparation of *Hyssopus officinalis* Extract

To 10 g of above-ground parts of *Hyssopus officinalis* (obtained from TOCHIMOTO TENKAIDO CO., LTD.), 100 mL of aqueous ethanol solution (50% by volume) was added, and then extraction was carried out for 7 days at room temperature under a stable condition. After that, the extract was obtained by performing filtration. The solid content concentration of the extract was 1.76% (w/v). The extract was diluted with aqueous ethanol solution (50% by volume), to be 1.00% (w/v) of the solid content concentration.

(13) Preparation of *Ribes nigrum* Extract

The *Ribes nigrum* extract powder (obtained from Kenko Corporation) which has been prepared from fruits of *Ribes nigrum* from Northern Europe was dissolved in an aqueous ethanol solution (50% by volume) to obtain the *Ribes nigrum* extract with solid content concentration of 1.00% (w/v).

(14) Preparation of *Vaccinium myrtillus* Extract

The *Vaccinium myrtillus* extract powder (obtained from Kenko Corporation) was dissolved in an aqueous ethanol solution (50% by volume) to obtain the *Vaccinium myrtillus* extract with solid content concentration of 1.00% (w/v).

(15) Preparation of *Artemisia princeps* Extract

The dried *Artemisia princeps* extract F (obtained from Maruzen Pharmaceuticals Co., Ltd.) which has been prepared by extraction from dried *Artemisia princeps* leaves with hot water was dissolved in an aqueous ethanol solution (20% by volume) to obtain the *Artemisia princeps* extract with solid content concentration of 1.00% (w/v).

(16) Preparation of *Haematoxylon campechianum* L. Extract

The logwood extract (trade name: HEMATEIN, obtained from ICHIMARU PHARCOS), which is an extract of *Haematoxylon campechianum* L., was dissolved in an aqueous ethanol solution (20% by volume) to obtain the *Haematoxylon campechianum* L. extract with solid content concentration of 1.00% (w/v).

2. Evaluation of Effect of Inhibiting Xanthine Oxidase and Effect of Inhibiting Uric Acid Production Hypoxanthine (manufactured by Wako Pure Chemical Industries, Ltd.; concentration: 100 μM/L) and a xanthine oxidase (originating from buttermilk; manufactured by Wako Pure Chemical Industries, Ltd.; concentration: 0.01 unit/mL) were dissolved in a sodium phosphate buffer solution (pH: 7.6; concentration in the reaction solution: 25 mM/L) to prepare a sample solution. To this sample solution, various extracts which had been prepared in the above preparative examples were added to have a concentration of 1% by volume, 0.1% by volume or 0.01% by volume, and then the components reacted with each other. After reaction of the reaction solution for 30 minutes at room temperature, 0.3 mol/L of perchloric acid was added in the amount that was the half of the amount of the reaction solution to terminate the reaction.

Upon the completion of the reaction, 0.2 mol/L of sodium dihydrogen phosphate was added in the amount that was the half of the amount of the reaction solution to give a sample for HPLC. The amount of the uric acid contained in the sample for HPLC was measured using the HPLC system (manufactured by SHIMADZU CORPORATION). Summary of the HPLC system is described below.

(Summary of HPLC System)
System Controller: SCL-10A (Trade Name, Manufactured by SHIMADZU CORPORATION)
Column oven: CTO-10A (trade name, manufactured by SHIMADZU CORPORATION)
Pump: LC-10AD (trade name, manufactured by SHIMADZU CORPORATION)
Auto-sampler: SIL-10A (trade name, manufactured by SHIMADZU CORPORATION)
Detector: SPD-10A (trade name, manufactured by SHIMADZU CORPORATION)

The above sample for HPLC in an amount of 50 μL was injected to a column (trade name: INERTSIL ODS-3 (particle diameter of 5 μm, inner diameter of 4.6 mm, and length of 250 mm, manufactured by GL Sciences Inc.)), and then eluted at a column temperature of 40° C. using an elution solution (5% methanol, 60 mM phosphoric acid, 14 mM disodium hydrogen phosphate (pH 2.2)) with a flow rate of 1.0 mL/min. By measuring the absorbance at 265 nm, the measurement of the uric acid amount produced was carried out.

As a control test, the production amount of uric acid was also measured by HPLC for the reaction solution not containing any of the above extracts.

The activity of inhibiting a xanthine oxidase (activity of inhibiting uric acid production) upon the addition of various extracts was calculated according to the following equation.

Activity of inhibiting a xanthine oxidase (xanthine oxidase inhibition rate) (%)=$\{(B-A)/B\} \times 100$ Herein, A indicates the production amount of uric acid when the above extract was added, and B indicates the production amount of uric acid when none of the above extracts was added.

Figure 1:
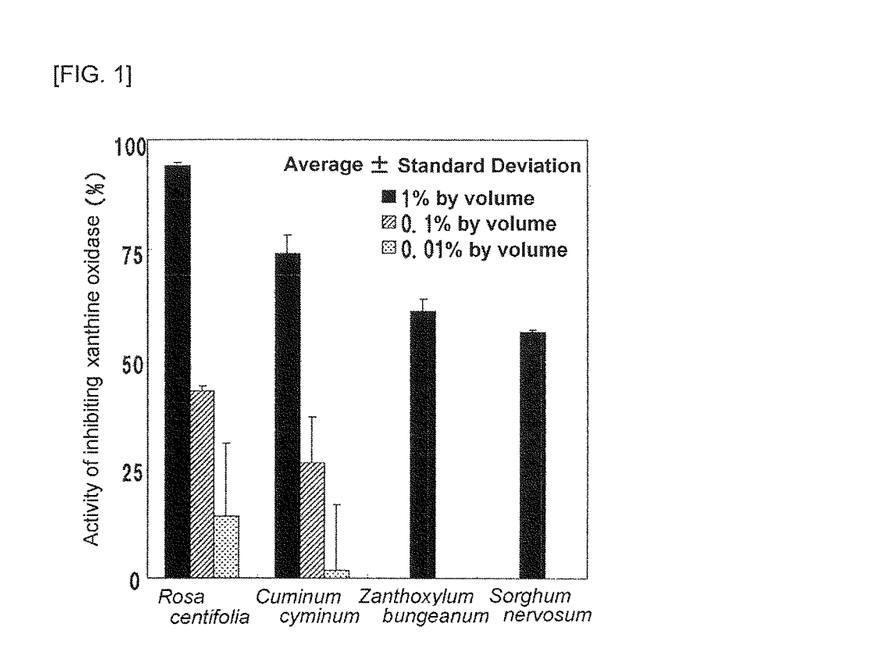
FIG. 1 is a diagram which illustrates xanthine oxidase inhibition rates when an extract of Rosa centifolia, Cuminum cyminum, Zanthoxylum bungeanum or Sorghum nervosum is added.
Figure 2:
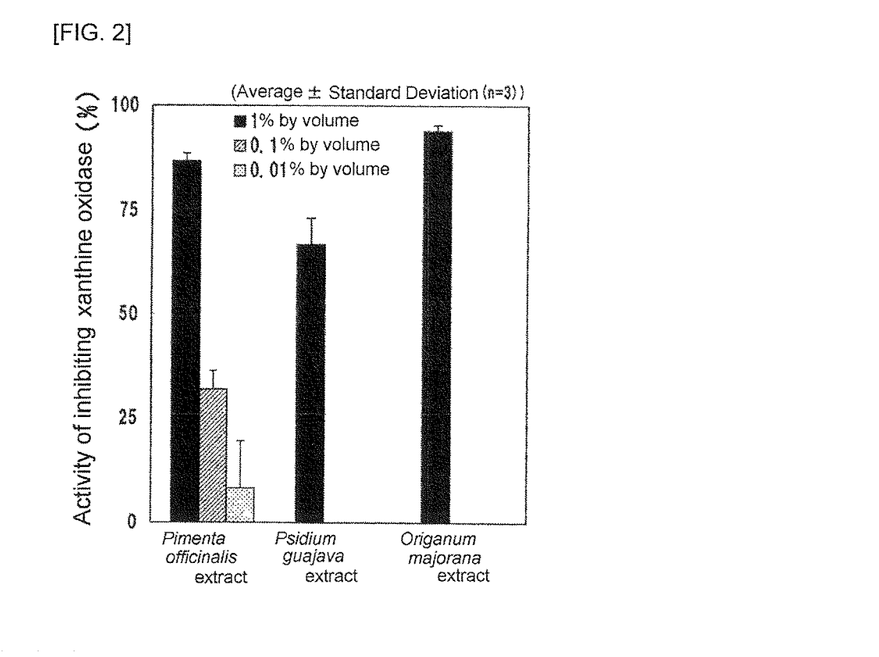
FIG. 2 is a diagram which illustrates xanthine oxidase inhibition rates when an extract of Pimenta officinalis, Psidium guajava or Origanum majorana is added.
Figure 3:
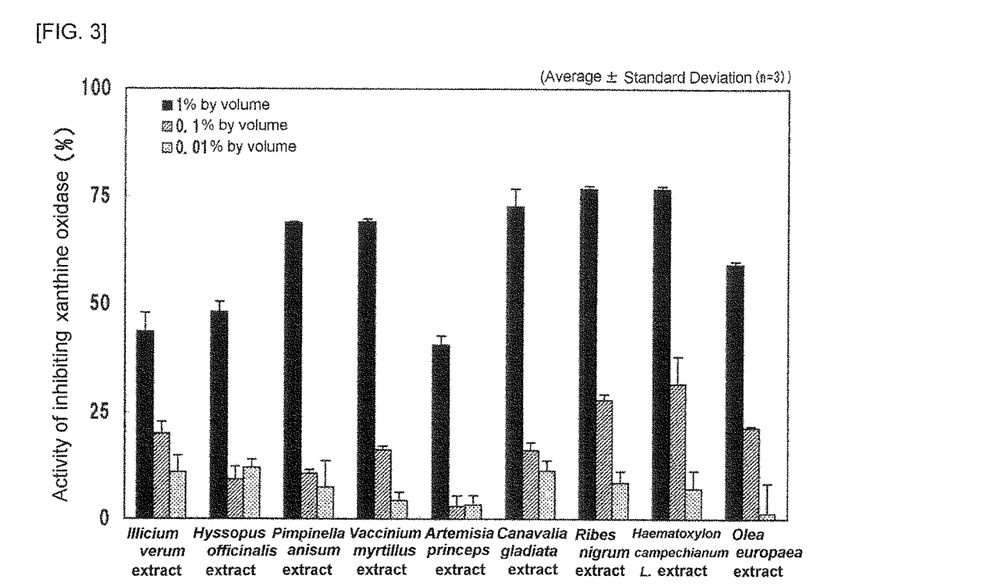
FIG. 3 is a diagram which illustrates xanthine oxidase inhibition rates when an extract of Illicium verum, Hyssopus officinalis, Pimpinella anisum, Vaccinium myrtillus, Artemisia princeps, Canavalia gladiata, Ribes nigrum, Haematoxylon campechianum L. or Olea europaea is added.

Results are shown in Table 1 and FIGS. 1 to 3.

TABLE 1

(Average ± Standard Deviation (n = 3))

| | Xanthine oxidase inhibition rate (%) | | |
|---|---|---|---|
| Kind of extract | 1% by volume | 0.1% by volume | 0.01% by volume |
| *Cuminum cyminum* | 74.0 ± 4.2 | 26.3 ± 10.1 | 1.7 ± 15.1 |
| *Rosa centifolia* | 94.0 ± 0.8 | 42.8 ± 1.2 | 14.1 ± 16.6 |
| *Zanthoxylum bungeanum* | 61.1 ± 2.7 | — | — |
| *Sorghum nervosum* | 56.3 ± 0.5 | — | — |
| *Pimenta officinalis* | 86.8 ± 1.8 | 31.9 ± 1.8 | 8.2 ± 11.4 |
| *Psidium guajava* | 66.7 ± 6.4 | — | — |
| *Origanum majorana* | 93.9 ± 1.5 | — | — |
| *Pimpinella anisum* | 68.8 ± 0.3 | 10.7 ± 0.9 | 7.5 ± 6.2 |
| *Olea europaea* | 59.2 ± 0.8 | 21.4 ± 0.3 | 1.3 ± 7.0 |
| *Illicium verum* | 43.6 ± 4.4 | 20.0 ± 2.8 | 10.9 ± 4.0 |
| *Canavalia gladiata* | 72.6 ± 4.2 | 16.1 ± 1.8 | 11.3 ± 2.4 |
| *Hyssopus officinalis* | 48.1 ± 2.4 | 9.3 ± 3.0 | 12.0 ± 1.9 |
| *Ribes nigrum* | 76.8 ± 0.7 | 27.9 ± 1.3 | 8.5 ± 2.6 |
| *Vaccinium myrtillus* | 69.0 ± 6.1 | 16.2 ± 0.9 | 4.4 ± 1.9 |
| *Artemisia princeps* | 40.5 ± 2.1 | 3.0 ± 2.5 | 3.3 ± 2.2 |
| *Haematoxylon campechianum* L. | 76.8 ± 0.7 | 31.7 ± 6.2 | 7.1 ± 4.1 |

As clearly shown in Table 1 and FIGS. 1 to 3, it was found that each of the extracts of *Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps* and *Haematoxylon campechianum* L. has an activity of inhibiting a xanthine oxidase and an activity of inhibiting uric acid production. In addition, it was also confirmed that no uric acid was produced in the reaction solution which did not contain the extract and the enzyme (i.e., xanthine oxidase).

Therefore, the xanthine oxidase inhibitor and the uric acid-producing inhibitor of the present invention were found to have an excellent effect of inhibiting an activity of a xanthine oxidase and an excellent effect of inhibiting production of uric acid, respectively.

3. Evaluation of an Effect of Preventing Hyperuricemia

SD male rats (6 week old; provided by Charles River Laboratories Japan Inc.) were bred in a stainless bracket breeding cage under the temperature of 23±2° C., humidity of 55±10%, and 12-hour light/dark cycle (light period: from 7:00 AM to 7:00 PM). During the breeding, the rats were fed with solid feeds for test animals (CE-2 solid feed, manufactured by CLEA Japan, Inc.) and tap water using an automatic water feeding machine with free access.

Onset of hyperuricemia in the rat was caused by slight modification of the method using oxonic acid, i.e., a hyperuricemia-inducing agent, as described in "Eur J Pharmacol," 1993, Vol. 241, No. 3, pp. 183-188 by Komoriya K. et al. Specifically, the rats were divided into five groups, each group having 5 animals with similar average body weight, yielding no oxonic acid administration group-1, oxonic acid administration control group-1, oxonic acid-*Cuminum cyminum* extract administration group, oxonic acid-*Zanthoxylum bungeanum* extract administration group, and oxonic acid-*Sorghum nervosum* extract administration group. Meanwhile, other rats different from the above were divided into three groups, each group having 5 animals with similar average body weight, yielding no oxonic acid administration group-2, oxonic acid administration control group-2 and oxonic acid-*Pimenta officinalis* extract administration group.

Animals of no oxonic acid administration group-1, oxonic acid administration control group-1, oxonic acid-*Cuminum cyminum* extract administration group, oxonic acid-*Zanthoxylum bungeanum* extract administration group and oxonic acid-*Sorghum nervosum* extract administration group were forced to fast for 12 hours. After that, the animals of the no oxonic acid administration group-1 were orally administered with 0.5 w/v % methylcellulose solution (400 cP, sterilized, manufactured by Wako Pure Chemical Industries, Ltd.) in a dosage of 5 mL/kg of body weight. To the groups other than the no oxonic acid administration group-1, potassium oxonate (manufactured by Sigma Aldrich Chemie Gmbh) dissolved in 0.5 w/v % methylcellulose solution to have the concentration of 500 mg/5 mL was orally administered in a dosage of 5 mL/kg of body weight. One hour after the administration of oxonic acid, to the groups of oxonic acid-*Cuminum cyminum* extract administration group, oxonic acid-*Zanthoxylum bungeanum* extract administration group and oxonic acid-*Sorghum nervosum* extract administration group, a freeze-dry product of *Cuminum cyminum* extract, a freeze-dry product of *Zanthoxylum bungeanum* extract or a freeze-dry product of *Sorghum nervosum* extract, which was dissolved in 0.5 w/v % methylcellulose solution to have the concentration of 4 g/20 mL, was orally administered in a dosage of 20 mL/kg of body weight, while other groups received oral administration of 0.5 w/v % methylcellulose solution in a dosage of 20 mL/kg of body weight. Three hours after the administration, 200 µL of blood was drawn from jugular vein while the animal was being anesthesized. Thus-obtained blood was transferred to a CapiJet Capillary Blood Collection Tube (trade name, purchased from TERUMO Corporation) and centrifuged at 3500×g for 5 minutes to separate blood serum. As a result, a sample for measuring the amount of uric acid in blood serum was obtained.

To 20 µL of this sample for measuring the amount of uric acid in blood serum, 200 µL of 0.3 mol/L perchloric acid was added. The resultant was allowed to stand on ice for 30 minutes and centrifuged at 20000×g for 20 minutes to obtain the supernatant. To 100 µL of the supernatant, 100 µL of 0.2 mol/L sodium dihydrogen phosphate was added to give a sample for HPLC. The amount of the uric acid contained in the sample for HPLC was measured using the HPLC system (manufactured by SHIMADZU Corporation). Summary of the HPLC system is described below.

(Summary of HPLC System)
System controller: SCL-10A (trade name, manufactured by SHIMADZU CORPORATION)
Column oven: CTO-10A (trade name, manufactured by SHIMADZU CORPORATION)
Pump: LC-10AD (trade name, manufactured by SHIMADZU CORPORATION)
Auto-sampler: SIL-10A (trade name, manufactured by SHIMADZU CORPORATION)
Detector: SPD-10A (trade name, manufactured by SHIMADZU CORPORATION)

The above sample for HPLC in an amount of 50 µL was injected to a column (trade name: INERTSIL ODS-3 (particle diameter of 5 µm, inner diameter of 4.6 mm and length of 250 mm, manufactured by GL Sciences Inc.)), and then eluted at a column temperature of 40° C. using an elution solution (5% methanol, 60 mM phosphoric acid, 14 mM disodium hydrogen phosphate (pH 2.2)) with a flow rate of 0.5 mL/min. By measuring the absorbance at 284 nm, the measurement of the uric acid contained in blood serum was carried out.

Figure 4:
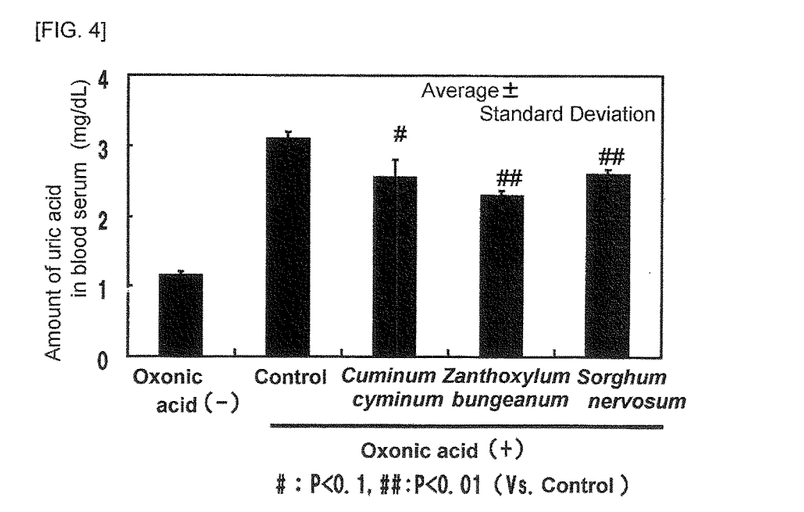
FIG. 4 is diagram which illustrates values of uric acid in blood serum when an extract of Cuminum cyminum, Zanthoxylum bungeanum or Sorghum nervosum was orally administered to induced hyperuricemic model rats.

The result is shown in FIG. 4.

As it is clearly shown in FIG. 4, it was found that the value of uric acid in blood serum increases by administration of potassium oxonate, i.e., a hyperuricemia-inducing agent. However, it was also found that, by administering the extract of *Zanthoxylum bungeanum, Sorghum nervosum* or *Cuminum cyminum*, the increase in the value of uric acid in blood serum resulting from the induced hyperuricemia is inhibited.

Furthermore, after forcing the fasting of the animals of the no oxonic acid administration group-2, the oxonic acid administration control group-2 and oxonic acid-allspice extract administration group for 12 hours, 200 µL of blood was drawn from jugular vein while the animal was being anesthesized. On hour after the drawing blood, the animals of the no oxonic acid administration group-2 were orally administered with 0.5 w/v % methylcellulose solution (400 cP, sterilized, manufactured by Wako Pure Chemical Industries, Ltd.) in a dosage of 5 mL/kg of body weight. To the groups other than the no oxonic acid administration group-2, potassium oxonate (manufactured by Sigma Aldrich Chemie Gmbh) dissolved in 0.5 w/v % methylcellulose solution to have the concentration of 500 mg/5 mL was orally administered in a dosage of 5 mL/kg of body weight. One hour after the administration of oxonic acid, to the group of oxonic acid-*Pimenta officinalis* extract administration group, a freeze-dry product of Pimenta officinalis extract, which was dissolved in 0.5 w/v % methylcellulose solution to have the concentration of 4 g/20 mL, was orally administered in a dosage of 20 mL/kg of body weight, while other groups received oral administration of 0.5 w/v % methylcellulose solution in a dosage of 20 mL/kg of body weight. One, two, three and six hours after the administration, 200 μL of blood was drawn from jugular vein while the animal was being anesthesized. Thus-obtained blood was transferred to a CapiJet Capillary Blood Collection Tube (trade name, purchased from TERUMO Corporation) and centrifuged at 3500×g for 5 minutes to separate blood serum. As a result, a sample for measuring the amount of uric acid in blood serum was obtained. By using these samples for measuring the amount of uric acid in blood serum, the amount of uric acid in blood serum was measured in the same manner as the above. The result is shown in FIG. 5.

Figure 5:
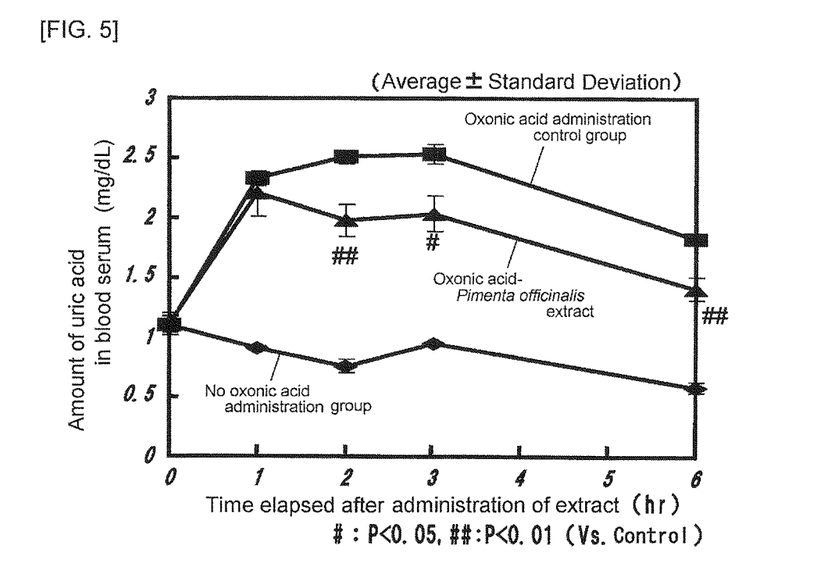
FIG. 5 is diagram which illustrates values of uric acid in blood serum when an extract of Pimenta officinalis was orally administered to induced hyperuricemic model rats.

As it is clearly shown in FIG. 5, it was found that the value of uric acid in blood serum increases by administration of potassium oxonate, i.e., a hyperuricemia-inducing agent. However, it was also found that, by administering the extract of Pimenta officinalis, the increase in the value of uric acid in blood serum resulting from the induced hyperuricemia is inhibited.

From the results shown above, it was found that the extract of each of Zanthoxylum bungeanum, Sorghum nervosum, Cuminum cyminum, Rosa centifolia, Pimenta officinalis, Origanum majorana, Psidium guajava, Pimpinella anisum, Olea europaea, Illicium verum, Canavalia gladiata, Hyssopus officinalis, Ribes nigrum, Vaccinium myrtillus, Artemisia princeps and Haematoxylon campechianum L. has an effect of inhibiting a xanthine oxidase, an effect of inhibiting uric acid production, and an effect of inhibiting an increase in a value of blood uric acid, as well as an effect of improving or preventing gout, hyperuricemia or a cardiovascular disease, or reducing their onset possibility. Therefore, the xanthine oxidase inhibitor, the uric acid-producing inhibitor and the agent for improving or preventing gout, hyperuricemia or a cardiovascular disease of the present invention are suitable for improvement or prevention of gout, hyperuricemia or a cardiovascular disease that is caused by abnormality in the metabolism of purine compounds by xanthine oxidase.

4. Production of the Agent for Improving or Preventing Gout, Hyperuricemia or a Cardiovascular Disease of the Present Invention Regarding the agent for improving or preventing gout, hyperuricemia or a cardiovascular disease of the present invention, a shell for a soft capsule preparation having the following composition was filled with 400 mg of soy bean oil and 100 mg of the ethanol extract of Sorghum nervosum or Pimenta officinalis according to a standard method to produce a soft capsule preparation.

| (Component) | (Content: mass %) |
|---|---|
| Gelatin | 70.0 |
| Glycerin | 22.9 |
| Methyl paraoxybenzoic acid | 0.15 |
| Propyl paraoxybenzoic acid | 0.51 |
| Water | 6.44 |

5. Production of the Beverage of the Present Invention

Regarding the beverage of the present invention, a beverage having the following composition was produced according to a standard method by using the ethanol extract of Sorghum nervosum or Pimenta officinalis.

| (Component) | (Content: mass %) |
|---|---|
| Powdered skim milk | 3.5 |
| Enzyme hydrolysate of milk casein | 3.5 |
| Fructose | 9.0 |
| Ethanol extract of Sorghum nervosum or Pimenta officinalis | 0.5 |
| Citric acid | 0.1 |
| Ascorbic acid | 0.1 |
| Perfume | 0.1 |
| Water | 83.2 |

INDUSTRIAL APPLICABILITY

The xanthine oxidase inhibitor of the present invention has an excellent effect of inhibiting a xanthine oxidase. Furthermore, the uric acid-producing inhibitor of the present invention has an excellent effect of inhibiting production of uric acid. Therefore, the xanthine oxidase inhibitor and the uric acid-producing inhibitor of the present invention can be used as an agent for improving or preventing gout, hyperuricemia or a cardiovascular disease or preventing their onset possibility, and also under the idea of having an effect of improving or preventing gout, hyperuricemia or a cardiovascular disease or preventing their onset possibility, they can be appropriately used for a functional food and beverage product, a food and beverage product for a patient, and a special health food and beverage product in which the point of use is indicated, if necessary.

Having described our invention as related to the present embodiments, it is our intention that the invention not be limited by any of the details of the description, unless otherwise specified, but rather be construed broadly within its spirit and scope as set out in the accompanying claims.

This non-provisional application claims priority under 35 U.S.C. §119 (a) on Patent Application No. 2008-177016 filed in Japan on Jul. 7, 2008, and Patent Application No. 2008-177017 filed in Japan on Jul. 7, 2008, each of which is entirely herein incorporated by reference.

What is claimed is:

1. A method of controlling or reducing a patient's blood uric acid level in a hyperuricemia patient in need of the same which comprises
   orally administering to the hyperuricemia patient a therapeutically effective amount of a Sorghum nervosum extract,
   wherein said extract is prepared by a method comprising extracting Sorghum nervosum with an extraction solvent selected from the group consisting of water, ethanol, and a mixture of water and ethanol.

2. The method of claim 1, wherein the dose of the extract that is administered to the patient is 0.001 to 10 g/kg of body weight per day.

3. The method of claim 1, wherein the patient's blood uric acid concentration is more than 7 mg/dL.

4. The method of claim 1, wherein the extraction solvent is water, or a mixture of water and ethanol that contains up to 50% ethanol.

5. The method of claim 1, wherein the hyperuricemia patient has gout or is in need of reducing the probability of developing gout.

6. The method of claim 5, wherein the dose of the extract that is administered to the patient is 0.001 to 10 g/kg of body weight per day.

7. The method of claim 5, wherein the patient's blood uric acid concentration is more than 7 mg/dL.

8. The method of claim 5, wherein the extraction solvent is water, or a mixture of water and ethanol that contains up to 50% ethanol.

9. The method of claim 5, wherein the hyperuricemia patient is in need of reducing the probability of developing gout.

\* \* \* \* \*